United States Patent
Thoniyot et al.

(10) Patent No.: US 11,534,375 B2
(45) Date of Patent: Dec. 27, 2022

(54) SOLVENT-FREE METHOD OF ENCAPSULATING A HYDROPHOBIC ACTIVE

(71) Applicant: Agency for Science, Technology and Research, Singapore (SG)

(72) Inventors: Praveen Thoniyot, Singapore (SG); Parijat Kanaujia, Singapore (SG); Alexander M. Van Herk, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 101 days.

(21) Appl. No.: 16/498,284

(22) PCT Filed: Mar. 27, 2018

(86) PCT No.: PCT/SG2018/050136
§ 371 (c)(1),
(2) Date: Sep. 26, 2019

(87) PCT Pub. No.: WO2018/182509
PCT Pub. Date: Oct. 4, 2018

(65) Prior Publication Data
US 2020/0179248 A1 Jun. 11, 2020

(30) Foreign Application Priority Data

Mar. 28, 2017 (SG) .......................... 10201702525X

(51) Int. Cl.
| | | |
|---|---|---|
| *A61K 8/11* | (2006.01) | |
| *A61K 8/02* | (2006.01) | |
| *A61K 8/90* | (2006.01) | |
| *A61K 9/107* | (2006.01) | |
| *A61K 9/51* | (2006.01) | |
| *A61K 45/06* | (2006.01) | |
| *A61Q 19/00* | (2006.01) | |
| *A01N 53/00* | (2006.01) | |

(52) U.S. Cl.
CPC .............. *A61K 8/11* (2013.01); *A61K 8/0287* (2013.01); *A61K 8/90* (2013.01); *A61K 9/1075* (2013.01); *A61K 9/5146* (2013.01); *A61K 45/06* (2013.01); *A61Q 19/00* (2013.01); *A01N 53/00* (2013.01); *A61K 2800/413* (2013.01); *A61K 2800/805* (2013.01)

(58) Field of Classification Search
CPC . A61K 8/90; A61K 8/11; A61K 8/345; A61K 9/1075; A61K 8/671; A61K 45/06; A61K 9/5146; A61K 8/0287; A61K 2800/413; A61K 2800/412; A61K 2800/805; A61K 2800/10; A61P 17/00; A61Q 19/00; A01N 53/00
See application file for complete search history.

(56) References Cited

U.S. PATENT DOCUMENTS

| | | | | |
|---|---|---|---|---|
| 5,665,428 A | * | 9/1997 | Cha .................. | A61K 38/38 427/213.3 |
| 2003/0180363 A1 | * | 9/2003 | Seo .................. | A61K 47/34 424/486 |
| 2010/0080852 A1 | * | 4/2010 | Beyerinck ........... | A61K 9/5169 424/501 |
| 2010/0330368 A1 | | 12/2010 | Prud'homme et al. | |
| 2013/0122058 A1 | | 5/2013 | Chow et al. | |
| 2013/0189315 A1 | | 7/2013 | Zale et al. | |
| 2013/0207286 A1 | * | 8/2013 | Pirot ................ | B01J 13/10 264/4.1 |
| 2014/0127271 A1 | | 5/2014 | Sill et al. | |
| 2014/0271884 A1 | * | 9/2014 | Prud'homme ....... | A61K 31/593 424/489 |
| 2016/0166513 A1 | * | 6/2016 | Liu .................. | A61K 9/5192 424/497 |

FOREIGN PATENT DOCUMENTS

| | | | | |
|---|---|---|---|---|
| CN | 101288641 A | 10/2008 | | |
| WO | 02085337 A1 | 10/2002 | | |
| WO | WO-2007081965 A2 | * 7/2007 | ............. | A01N 25/10 |
| WO | 2015053716 A1 | 4/2015 | | |

OTHER PUBLICATIONS

Lee et al. Journal of Physics and Chemistry, 69, 2008, 1596-1599. (Year: 2008).*
Dong et al. Colloid and Surfaces A; Physicochem. Eng. Aspects, 358, 2010, 128-134. (Year: 2010).*
International Search Report for International Application No. PCT/SG2018/050136 dated Jun. 4, 2018, pp. 1-5.
Written Opinion of the International Searching Authority for International Application No. PCT/SG2018/050136 dated Jun. 4, 2018, pp. 1-7.
International Preliminary Report on Patentability for International Application No. PCT/SG2018/050136 dated May 31, 2019, pp. 1-25.
Windbergs, "Biodegradable Core—Shell Carriers for Simultaneous Encapsulation of Synergistic Actives," Journal of the American Chemical Society, vol. 135, 2013, pp. 7933-7937.
Foster Delivery Science, "Foamed Hot Melt Extrusion for Solid Molecular Dispersions," http://www.deliveryscience.com/content/foamed-hot-melt-extrusion-solid-molecular-dispersions, 2020, pp. 1-8.

(Continued)

*Primary Examiner* — Doan T Phan
(74) *Attorney, Agent, or Firm* — Shackelford, Bowen, McKinley & Norton, LLP

(57) ABSTRACT

Present disclosure relates to a solvent-free method of encapsulating a hydrophobic active in personal care, hydrophobic active in crop protection or a hydrophobic active pharmaceutical ingredient (API) in polymeric nanoparticles. The method includes mixing the hydrophobic active in a polymer melt, wherein the polymer melt comprises a melt of a block co-polymer, wherein the polymer melt acts as a solvent for the hydrophobic active. The method further includes maintaining the polymer melt in water for sufficient time to allow self-assembly of the block co-polymer to encapsulate the hydrophobic active therein.

16 Claims, 8 Drawing Sheets

(56) References Cited

OTHER PUBLICATIONS

Sakai-Kato et al., "General Considerations Regarding the in Vitro and in Vivo Properties of Block Copolymer Micelle Products and their Evaluation," Journal of Controlled Release, vol. 210, 2015, pp. 76-83.

Kataoka et al., "Block Copolymer Micelles for Drug Delivery: Design, Characterization and Biological Significance," Advanced Drug Delivery Reviews, vol. 47, 2001, pp. 113-131.

Anne Ammala, "Biodegradable Polymers as Encapsulation Materials for Cosmetics and Personal Care Markets," International Journal of Cosmetic Science, vol. 35, 2013, pp. 113-124.

Kumari et al., "Biodegradable Polymeric Nanoparticles Based Drug Delivery Systems," Colloids and Surfaces B: Biointerfaces, vol. 75, 2010, pp. 1-18.

Market Research Engine, "Global Microencapsulation Market Research Report—Industry Analysis, Size, Share, Growth, Trends and Forecast, 2018-2024," 2020, pp. 1-6.

Gindy et al., "Composite Block Copolymer Stabilized Nanoparticles: Simultaneous Encapsulation of Organic Actives and Inorganic Nanostructures," Langmuir, vol. 24, 2008, pp. 83-90.

Shibasaki et al., "Activated Monomer Cationic Polymerization of Lactones and the Application to Well-Defined Block Copolymer Synthesis with Seven-Membered Cyclic Carbonate," Macromolecules, vol. 33, 2000, pp. 4316-4320.

Rajendar Reddy Mallepally, "Encapulsation and Controlled Release of Pharmaceuticals with Biodegradable Hyperbranched Polyesters," Dissertation, 2009, pp. 1-145.

Lee et al., "Solvent-Free Preparation of Caprolactone Oligomer Microspheres," Journal of Physics and Chemistry of Solids, vol. 69, 2008, pp. 1596-1599.

Basak et al., "Encapsulation of Hydrophobic Drugs in Pluronic F127 Micelles: Effects of Drug Hydrophobicity, Solution Temperature, and pH," Langmuir, vol. 29, 2013, pp. 4350-4356.

Dong et al., "Self-Assembled Biodegradable Micelles Based on Star-Shaped PCL-b-PEG Copolymers for Chemotherapeutic Drug Delivery," Colloids and Surfaces A: Physicochemical and Engineering Aspects, vol. 358, No. 1-3, Jan. 25, 2010, pp. 128-134.

\* cited by examiner

SOLVENT-FREE METHOD OF ENCAPSULATING A HYDROPHOBIC ACTIVE

CROSS-REFERENCE TO RELATED APPLICATION

This application claims the benefit of priority of Singapore Patent Application No. 10201702525X, filed Mar. 28, 2017, the contents of which being hereby incorporated by reference in its entirety for all purposes.

TECHNICAL FIELD

The invention relates generally to a solvent-free method of encapsulating a hydrophobic active, and in particular, to an organic solvent-free encapsulation of hydrophobic actives in biodegradable particles using low melting co-polymers.

BACKGROUND

Self-assembly of block co-polymers as micelles, nanoparticles or vesicles constitutes one of the most actively researched methods in encapsulation technology. Majority of the actives in medicine and consumer care are hydrophobic in nature and majority of the methods use water miscible organic solvents such as tetrahydrofuran (THF) or dimethylformamide (DMF) to produce encapsulated nanoparticles. Such anti-solvent approaches using an organic solvent leads to huge problems in scalability of preparation and post-processing approaches that require the removal of solvents and leads to complications of particle aggregation and loss of integrity of the encapsulate structure. Alternatively, there are solvent-free approaches involving the use of double emulsion droplets for the formation of core-shell structures in a micro capillary device. This approach produces only micron-sized particles and obtaining sub-micron particles could be very challenging. An organic solvent-free approach will be an ultimate technological solution leading to reduction in toxic contamination and enhancement in scalability. Solvent-free processes for encapsulation will have a disruptive impact in medical and consumer care technology since both the industries produces very large number of encapsulates. The current practices are mostly solvent-based approach and the industry is spending lot of time and money in processes for solvent removal and analysis.

Therefore, there remains a need to provide for a solvent-free method that overcomes, or at least alleviates, the above drawbacks.

SUMMARY

Present disclosure describes a simple, efficient and versatile method to produce a sustainable and environmentally friendly encapsulation in the sub-micron size range without the use of organic solvent and would provide the required scalability and economic advantages for further technology development. In brief, the method involves an organic solvent-free process to encapsulate an active compound in an amphiphilic block co-polymer nanoparticle by dispersing single phase melts of the polymer and active. The block co-polymer undergoes self-assembly in water from a melt to encapsulate actives to form a nanoparticle.

The method affords the encapsulation of diverse types of hydrophobic actives (versatility), is a completely organic solvent-free approach (sustainability, economic), enables a high loading of active possible compared to existing solvent-based encapsulation techniques (efficacy), results in a high particle concentration without post-processing steps (sustainability), is a water-based technology (environmentally friendly), and produces sub-micron sized biodegradable particles with controlled release potential (usability).

Thus, according to one aspect of the disclosure, there is provided a solvent-free method of encapsulating a hydrophobic active in personal care, hydrophobic active in crop protection or a hydrophobic active pharmaceutical ingredient (API) in polymeric nanoparticles. The method includes mixing the hydrophobic active in a polymer melt, wherein the polymer melt comprises a melt of a block co-polymer, wherein the polymer melt acts as a solvent for the hydrophobic active. The method further includes maintaining the polymer melt in water for sufficient time to allow self-assembly of the block co-polymer to encapsulate the hydrophobic active therein.

According to another aspect of the disclosure, there is provided hydrophobic active pharmaceutical ingredient encapsulated polymeric nanoparticles formed by a method of the earlier aspect.

According to a further aspect of the disclosure, there is provided an aqueous, spray dried or freeze dried formulation comprising hydrophobic active pharmaceutical ingredient encapsulated polymeric nanoparticles formed by a method of the earlier aspect for use as a pharmaceutical or personal care product.

BRIEF DESCRIPTION OF THE DRAWINGS

In the drawings, like reference characters generally refer to the same parts throughout the different views. The drawings are not necessarily drawn to scale, emphasis instead generally being placed upon illustrating the principles of various embodiments. In the following description, various embodiments of the invention are described with reference to the following drawings.

DESCRIPTION

The following detailed description refers to the accompanying drawings that show, by way of illustration, specific details and embodiments in which the invention may be practised. These embodiments are described in sufficient detail to enable those skilled in the art to practise the invention. Other embodiments may be utilized and structural, chemical, and material changes may be made without departing from the scope of the invention. The various embodiments are not necessarily mutually exclusive, as some embodiments can be combined with one or more other embodiments to form new embodiments.

Since many hydrophobic actives and low melting block co-polymers are practically insoluble in cold water but dissolve in an appreciably amount at temperatures above the polymer melting temperature, it should be possible, though not necessarily so, to cool them down to a stabilized nanoparticle form if proper interactions are ensured between the actives and the polymers.

Under such conditions, organic solvent-free encapsulation of a hydrophobic active could be achieved, using water as a self-assembling medium without the necessity of an organic solvent. Here, the polymer itself could be used as a solvent for the actives. The self-assembly may take place spontaneously in water under ambient conditions (i.e. thermodynamically favoured assembly). Nevertheless, a temperature gradient and/or agitation can be used to accelerate the assembly of the high temperature polymer solution of the actives into encapsulated nanoparticles. In other words, no mechanical agitation or any other form of energy may be necessary for the self-assembly, which may take place even at room temperature. Increased temperature and/or use of agitation or sonication are simply to speed up the self-assembly.

Figure 1:
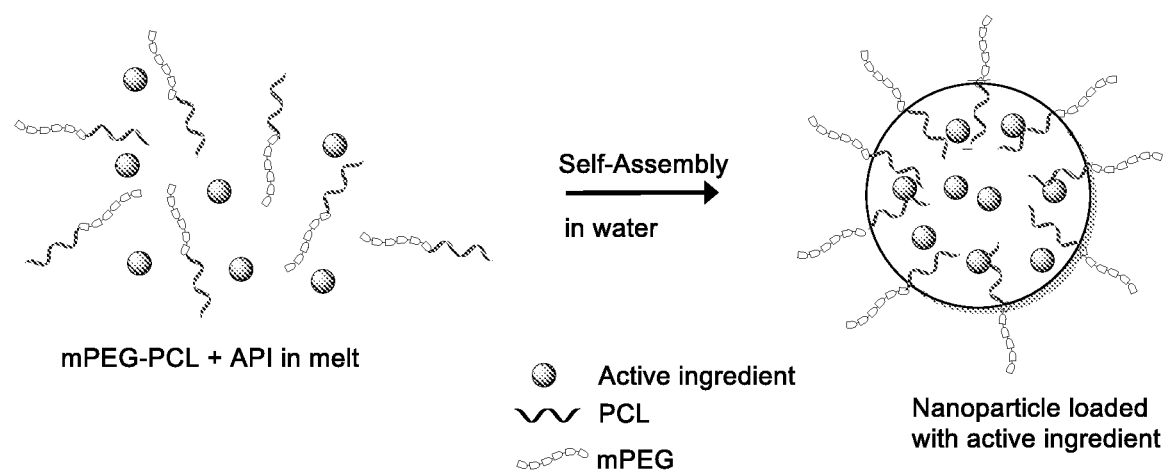
FIG. 1 shows a scheme of present strategy for the encapsulation by polymer self-assembly that eliminates the need of an organic solvent.

FIG. 1 shows a scheme of present overall strategy for the encapsulation by polymer self-assembly that eliminates the need of an organic solvent:—
a) solubilizing the active (API) in the polymer melt consisting of the active and block co-polymer; and
b) dispersing the active-polymer melt in water to trigger the self-assembly of the block co-polymer to thereby encapsulate the active.

Thus, according to one aspect of the disclosure, there is provided a solvent-free method of encapsulating a hydrophobic active in personal care, hydrophobic active in crop protection or a hydrophobic active pharmaceutical ingredient (API) in polymeric nanoparticles. It is to be understood that a solvent-free method refers to a method where the use of an organic solvent is omitted.

The method includes mixing the hydrophobic active in a polymer melt, wherein the polymer melt comprises a melt of a block co-polymer, and wherein the polymer melt acts as a solvent for the hydrophobic active. In other words, the hydrophobic active dissolves in the polymer melt. The hydrophobic active may dissolve partially or completely in the polymer melt.

The co-polymers preferably have low melting points and the hydrophobic block should be compatible with the active to be encapsulated. The co-polymers should solubilize the active in the melt. Alternatively or additionally, a stabilizer or solubilizer may be added to the polymer melt to stabilize the mixture of polymer melt and hydrophobic active.

In various embodiments, the block co-polymer may include a diblock co-polymer of poly (ethylene glycol)-polylactic acid, poly(ethylene glycol-poly(glycolic acid), poly (ethylene glycol)-poly-lactic-co-glycolic acid, poly(ethylene glycol)-poly(butyl cyano-acrylate), poly(ethylene glycol)-block-poly hydroxybutyrate), poly (ethylene glycol)-poly-(hydroxypropionate), poly-(ethylene glycol)-(Valero lactone), poly(ethylene glycol)-poly(caprolactone) (PEG-PCL), poly-(ethylene glycol)-poly-(benzyl aspartate), poly-(ethylene glycol)-poly-(benzyl glutamate), poly (ethylene glycol)-poly-benzyloxy trimethylene carbonate, poly(ethylene glycol)-poly-butadiene, poly(ethylene glycol)-poly-(butyl acrylate), or a tri-block copolymer of any one of the above hydrophobic and hydrophilic components.

In certain embodiments, the block co-polymer may include a PEG block.

In preferred embodiments, the block co-polymer may include a PEG block of 1,500 to 15,000 Da.

In alternative embodiments, the block co-polymer may include a PCL block.

In preferred embodiments, the block co-polymer may include a PCL block of 3,500 to 24,000 Da.

In various embodiments, the hydrophobic active may include a compound in various therapeutic classes selected from the group consisting of beta-adrenoceptor blocking agents, contrast media, corticosteroids, cough suppressants, diagnostic agents, diagnostic imaging agents, diuretics, dopaminergics, haemostatics, immuriological agents, lipid regulating agents, muscle relaxants, parasympathomimetics, parathyroid calcitonin, prostaglandins, radio-pharmaceuticals, sex hormones, anti-allergic agents, stimulants, sympathomimetics, thyroid agents, vasodilators, xanthines, analgesics, anti-inflammatory agents, anthelmintics, antiarrhythmic agents, antibiotics, anticoagulants, antidepressants, antidiabetic agents, antiepileptics, antihistamines, antihypertensive agents, antimuscarinic agents, antimycobacterial agents, antineoplastic agents, immunosuppressants, antithyroid agents, antiviral agents, anxiolytic sedatives and astringents.

For example, the hydrophobic active may be ibuprofen, fenofibrate, ketoconazole, PM2 peptide, or citronellal, Itraconazol, isotretionoin, β-carotene, retinal, retinoic acid, curcumin, doxorubicin, SN-38, paclitaxel, camptothecin, cisplatin, daunorubicin, methotrexate, mitomycin C, docetaxel, vincristine, amphotericin B, nystatin, prostaglandins, cyfluthrin, butanilicaine, fomocaine, isobutambene, lidocaine, risocaine, pseudococaine, prilocaine, tetracaine, trimecaine, tropacocaine, etomidate, metixen, profenamine, alimenazine, binedaline, perazine, chlorpromazine, fenpentadiol, fenanisol, mebenazine, methylphenidate, thioridazine, toloxaton, trimipramide, dimethadion, nicethamide, butoconazole, chlorphenesin, etisazole, exalamid, precilocine, miconazole, butibufen, azinphosphomethyl, cypermethrine, substituted phenyl thiophosphates, fenclophos, permethrine, piperonal, tetramethrine and/or trifluraline, viquidile, asperline, chlorambucile, mitotane, estramustine, taxol, penclomedine, trofosfamide, capsaicine, methylnicotinate, nicolclonate, oxprenolol, pirifibrate, simfibrate, thiadenol, aminopromazine, caronerine, difemerine, fencarbamide, tiropramide, moxaverine, testosterone enantate, testosterone-(4-methylpentanoate), azaperone, buramate, arildon, retinol, retinol acetate, retinol palmitate, tocopherol acetate, tocopherol succinate, tocopherol nicotinate, menadione, cholecalciferol, acephate bamifylline, alprenolol, butobendine, clordiazole, hexobendine, nicofibrate, penbutolol, pirmenol, prenylamine, procaine amide, propatrylnitrate, suloctidil, toliprolol, xidbendol, viquidile, asperline, chlorambucile, mitotane, estramustine, taxol and macrolide antibiotics.

In alternative embodiments, the hydrophobic active may include a crop protecting agent or a personal care agent.

In one embodiment, the crop protecting agent may include pyrethrins.

The method further includes maintaining the polymer melt in water for sufficient time to allow self-assembly of the block co-polymer to encapsulate the hydrophobic active therein. In other words, the self-assembly is a thermodynamically favoured process. The self-assembly may take place at room temperature. Alternatively, to speed up the self-assembly, the polymer melt may be maintained in water at above the room temperature, such as up to 85° C.

In preferred embodiments, the method may further include cooling the self-assembled dispersion to enhance the stabilization of the hydrophobic active encapsulated in the polymeric nanoparticles.

In various embodiments, the hydrophobic active may be dissolved at a temperature above the melting temperature of the block co-polymer. For example, the hydrophobic active may be dissolved at at least 1° C. above the melting temperature of the block co-polymer. The melting temperature of the block co-polymer is apparent to a person skilled in the art and may include known data from established publication or books.

In various embodiments, the polymer melt may be dispersed in water at 0 to 50° C. higher than the melting temperature of the block co-polymer.

In various embodiments, the polymer melt may be maintained in water at 50° C. or lower.

It may be advantageous to subsequently cool down the polymer melt to aid storage and to enhance stabilization of the nanoparticles formed. Thus, in certain preferred embodiments, the polymer melt may be cooled to room temperature and below to aid storage and to enhance stabilization of the nanoparticles formed. For example, the polymeric nanoparticles formed may be cooled to room temperature. In one embodiment, encapsulated citronellal formed by cooling to room temperature remains stable over a period of more than six months.

The cooling of the polymer melt may be carried out gradually. For example, the polymer melt may be cooled at a rate of about 0.25 to 1.5° C./min, such as 0.25, 0.3, 0.35, 0.4, 0.45, 0.5, 0.55, 0.6, 0.65, 0.7, 0.75, 0.8, 0.85, 0.9, 0.95, 1, 1.05, 1.1, 1.15, 1.2, 1.25, 1.3, 1.35, 1.4, 1.45, or 1.5° C./min.

In an attempt to enhance or speed up the self-assembly process, the method may further include stirring the dispersion of the polymer melt in water. For example, the dispersion may be stirred at a stirring rate of 50 rpm or higher.

After the formation of the hydrophobic active encapsulated polymeric nanoparticles, the nanoparticles may be separated from the polymer melt, for example, by ultracentrifugation, ultrafiltration, spray drying or freeze drying.

In certain embodiments, it may be advantageous to additionally include in the polymer melt a homo-polymer to aid or further accelerate the self-assembly process. For example, the homo-polymer may be, but not limited to, poly(ethylene glycol) (PEG), poly(lactic acid) (PLA), poly(glycolic acid) (PGA), or poly(caprolactone) (PCL). In one example, PEG may be additionally included in a polymer melt of PEG-PCL to further accelerate the encapsulation process.

The hydrophobic active pharmaceutical ingredient encapsulated polymeric nanoparticles formed by the above method may be employed as an aqueous, spray dried or freeze dried formulation. The formulation may be suitable for use as a pharmaceutical or personal care product.

In order that the invention may be readily understood and put into practical effect, particular embodiments will now be described by way of the following non-limiting examples.

EXAMPLES

Polymer Synthesis and Characterization

PEG-PCL diblock co-polymer are herein synthesized, with fixed PEG part at 5,000 Da and varied PCL ranging from 3,500 to 15,000 Da by acid-catalysed ring-opening polymerization of ε-caprolactone (CL) using monomethoxy poly(ethylene glycol) (mPEG) as an initiator. Drying of mPEG was achieved by azeoprotic distillation using toluene. It was then dissolved in dry dichloromethane and to this required amount of freshly distilled PCL was added and stirred under dry conditions. To this catalytic amount of hydrochloric acid in diethyl ether was added to catalyse the polymerization. Polymerization reaction mixture was stirred at room temperature for 24 h. The co-polymer was precipitated into hexane (two times), filtered, and dried at 45° C. in a vacuum oven. The results of each polymerization reaction and the resultant block lengths obtained by NMR and GPC are shown in Table 1 below.

TABLE 1

Different polymers used for the study and their molecular weight by NMR and GPC.

| Name of Polymer | Block ratios as shown by NMR | GPC Mn | GPC Mw | GPC PDI |
|---|---|---|---|---|
| mPEG-b-PCL | mPEG(5000)-b-PCL(7980) | 15042 | 19520 | 1.3 |
| mPEG-b-PCL | mPEG(5000)-b-PCL(13930) | 7997 | 13378 | 1.6 |
| mPEG-b-PCL | mPEG(5000)-b-PCL(7498) | 10395 | 12674 | 1.21 |
| mPEG-b-PCL | mPEG(5000)-b-PCL(11000) | 9697 | 12933 | 1.34 |
| mPEG-b-PLGA | mPEG(5000)-b-PLGA(7000) | 9836 | 15776 | 1.60 |

Figure 2:
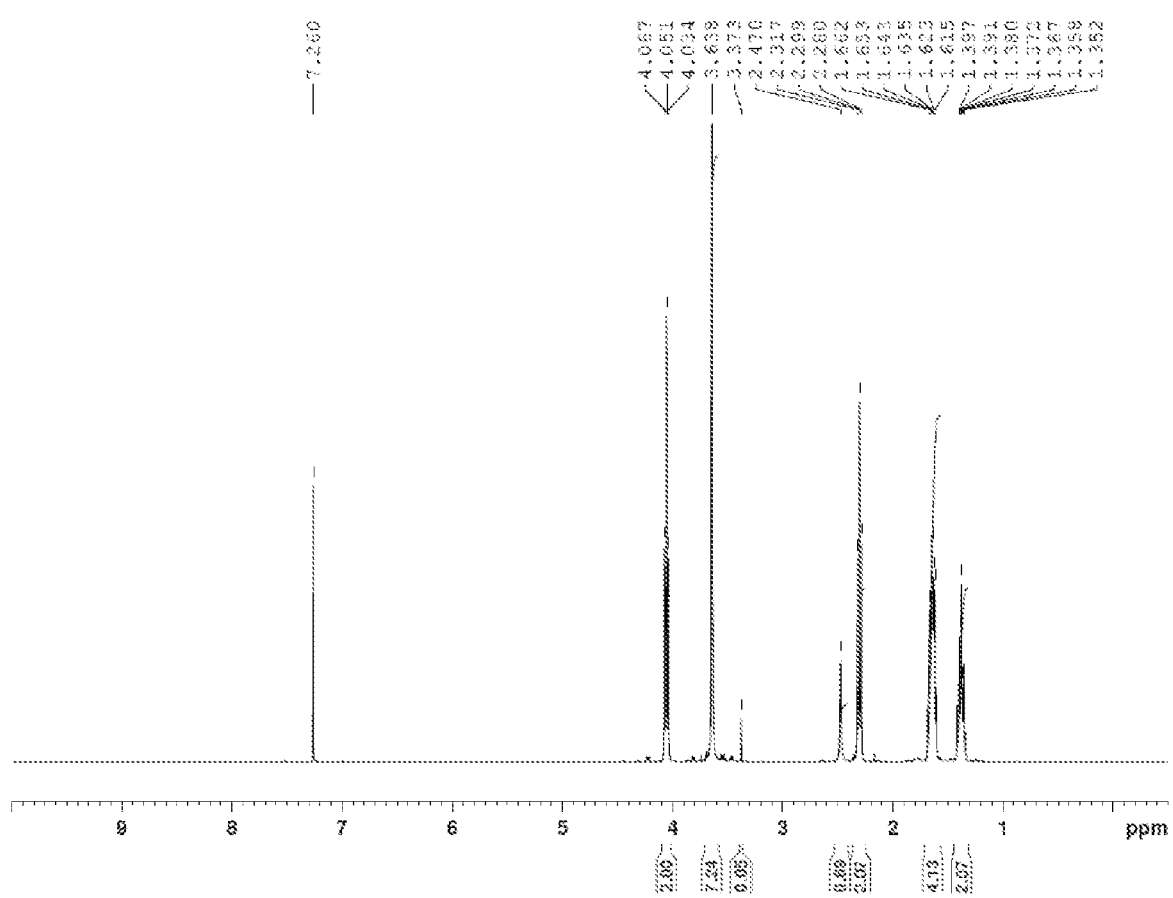
FIG. 2 shows 1H NMR spectrum of mPEG(5000)-b-PCL (7980) according to one example.

The synthesized polymers were analysed by 1H NMR spectrum and GPC. A typical spectrum is given in FIG. 2. Integrating the peak around δ 3.64 (corresponding to PEG block 4Hs) and comparing it with sum of the all the integrals of CH2 (PECL block, 10H) enables the calculation of molecular weight from the NMR spectra.

Figure 3:
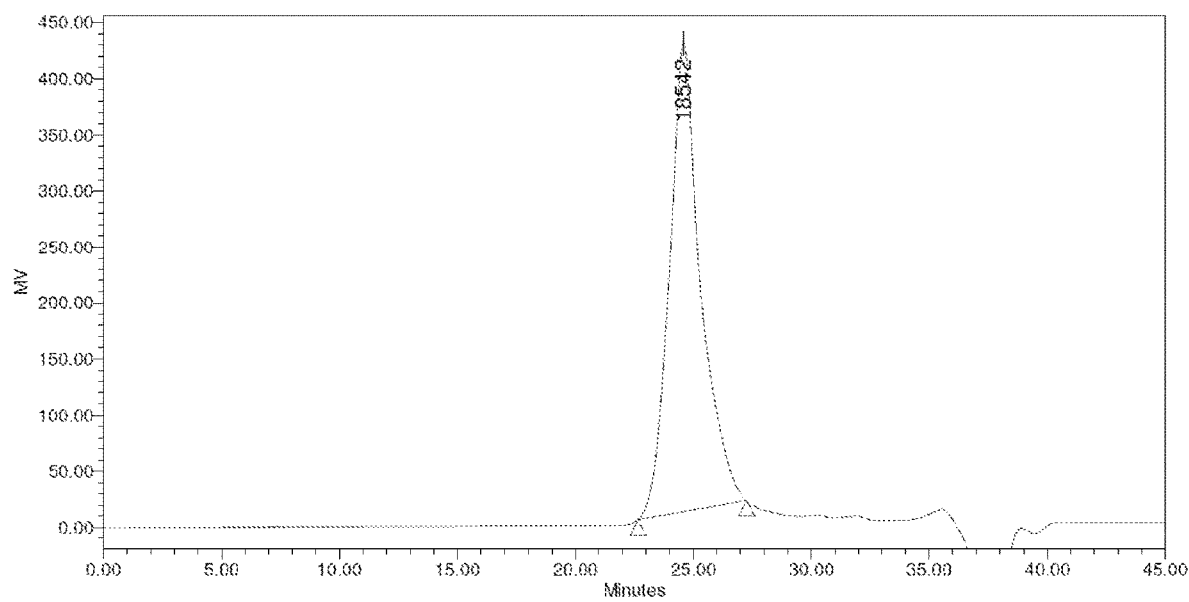
FIG. 3 shows gel permeation chromatogram (GPC) of mPEG(5000)-b-PCL(7980) according to one example.

A typical GPC result is shown in FIG. 3. The profile indicates mono modal distribution of chain lengths indicating that reactions were initiated by mPEG and not residual water in the system. All the polymers synthesized showed good polydispersity.

Thermogravimetric Analysis of Block Co-Polymers and APIs

Figure 4:
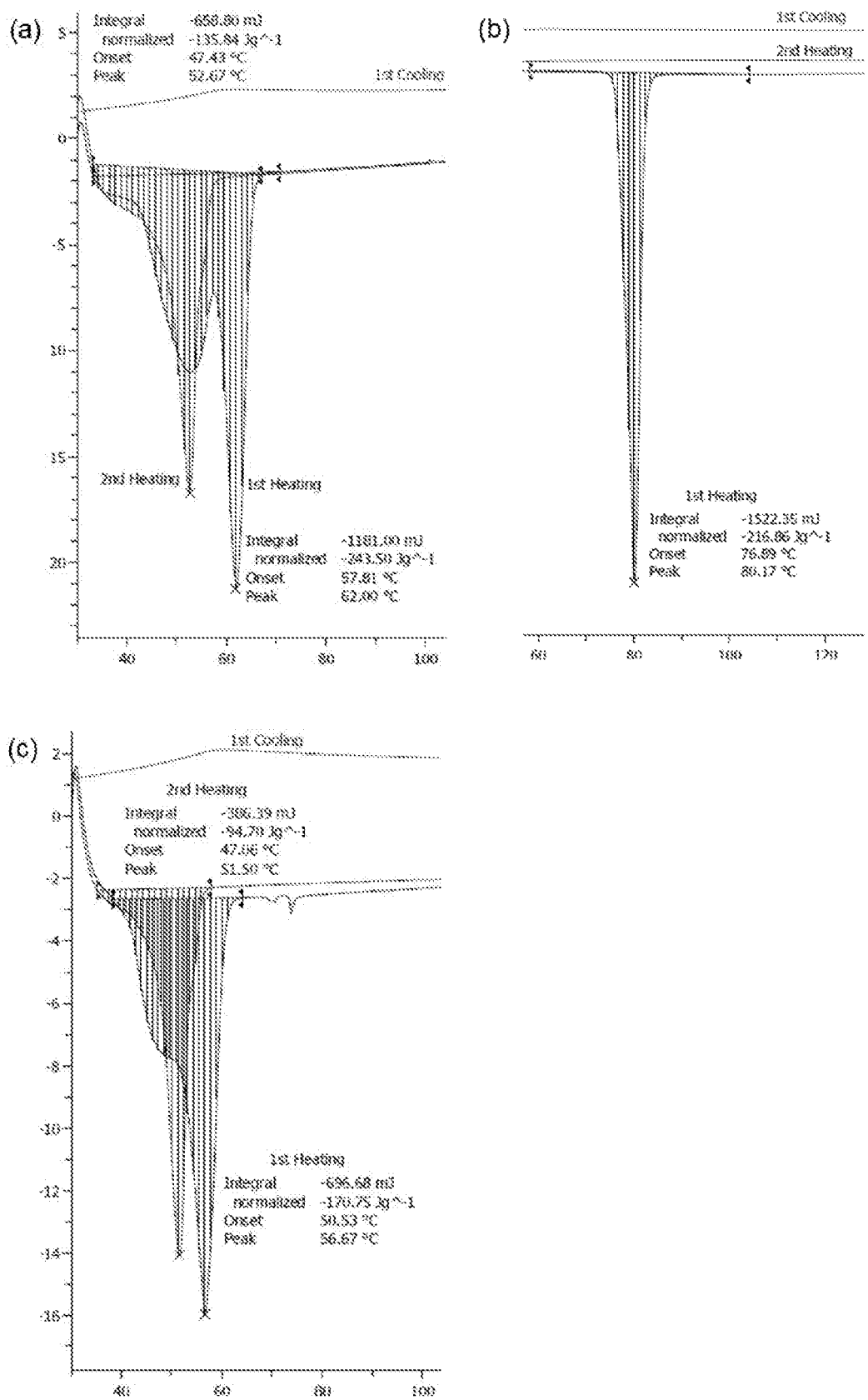
FIG. 4 shows thermograms of a) mPEG(5000)-b-PCL (7980), b) Pure Ibuprofen, and c) mPEG(5000)-b-PCL (7980)+20 wt % Ibuprofen ground together in mortar.

The thermogravimetric behaviour of the PEG-PCL in the presence and absence of the active were analyzed. A typical thermogram for the polymer, API and the blend is shown in FIG. 4. The pure block co-polymer mPEG(5000)-b-PCL (7980) gave a melting value of 57.81° C. for the PEG block and 62.00° C. for PCL block. In the second heating cycle, PEG melting shifted to 47.43° C. and PCL melting peak is shifted to 52.67° C., indicating that in the time frame of the experiment, both PEG and PCL fraction of the polymer were not able to relax back into the original solid state most likely due chain entanglements decreasing the melting of each fragment. Ibuprofen gave a sharp melting peak at 80.17° C. typical of pure small molecule. However, in the blend of PEG-PCL and Ibuprofen, the second cycle showed complete absence of Ibuprofen melting peak, showing that the API dissolved in the polymer melt at this temperature. This analysis was repeated for other APIs and the results are shown in Table 2.

TABLE 2

Melting behaviour of PEG-PCL in presence of various actives.

| No. | Polymer | Melting of PCL fragment Cycle 1 and Cycle 2 | API | API melting point | Melting of PCL in Polymer + API blend Cycle 1 and Cycle 2 |
|---|---|---|---|---|---|
| 1 | PEG-PCL | 62.00 52.67 | Ibuprofen | 80.17 | 56.67 51.50 |
| 2 | PEG-PCL | 62.00 52.67 | Fenofirbate | 82.50 | 57.17 50.00 |
| 3 | PEG-PCL | 62.00 52.67 | Ketoconazol | 150.33 | 62.67 55.17 |

From the thermogravimetric data, it is clear that PEG-PCL is a suitable polymer for encapsulating hydrophobic APIs such as Ibuprofen and Fenofibrate. In all the cases the second heating cycle did not show the melting peak of the API, indicating that it was dissolved in the polymer melt. This could form the first condition to be met for the solvent-free encapsulation of the actives. With a clear indication of solubilization of the API in the polymer melt, the encapsulation studies were conducted next.

Solvent-Free Encapsulation and Characterization

Figure 5:
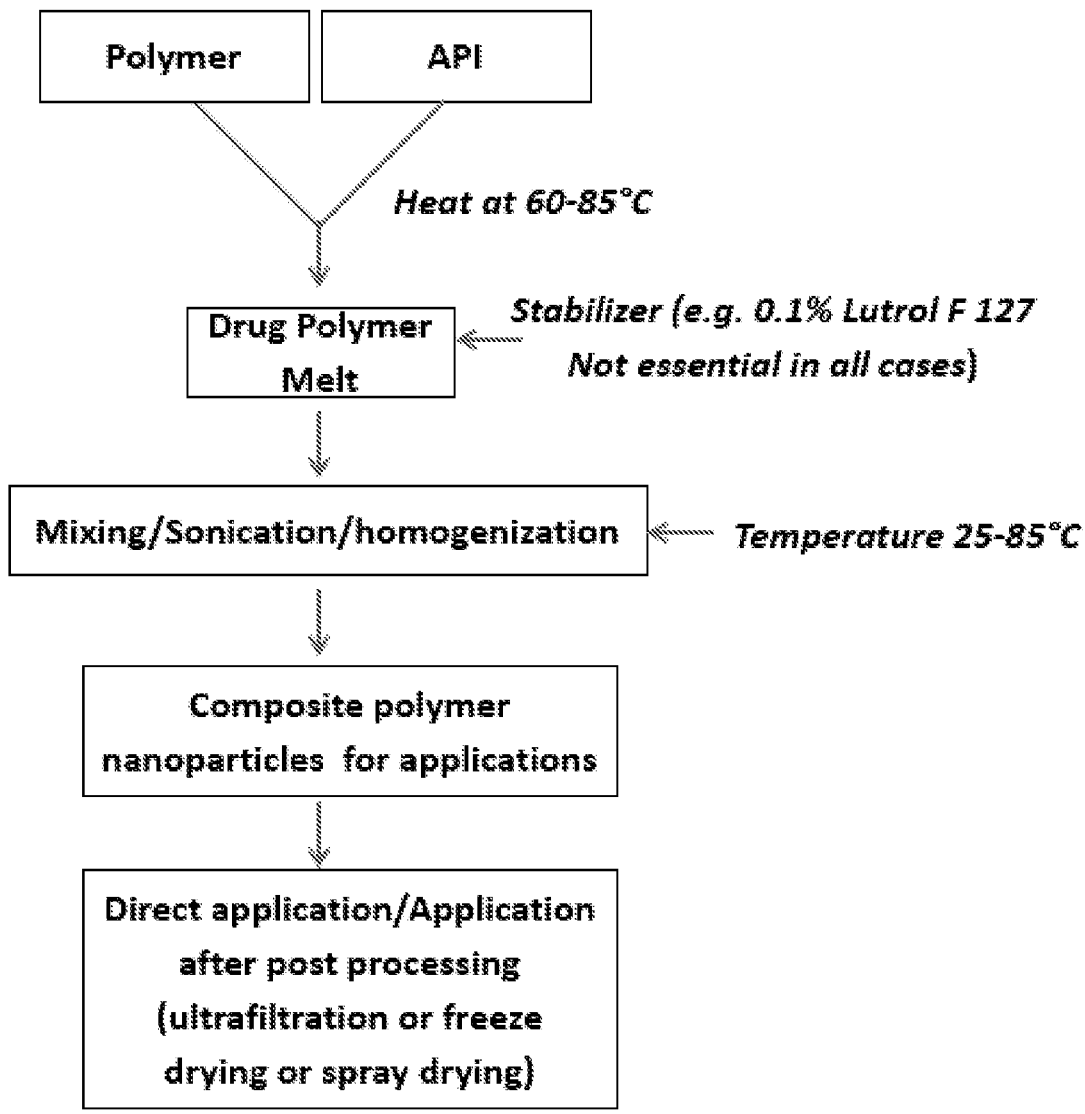
FIG. 5 shows a scheme of encapsulation of an active pharmaceutical ingredient by solvent-free approach according to one example.

Scheme for a typical encapsulation experiment using a hydrophobic active compound such as Ibuprofen is given in FIG. 5. The simplicity of the approach is very clear from this scheme. In a typical procedure, the hydrophobic active compound and polymer are ground together in a mortar and transferred to a small ampule where it is melted by heating, for example, in an oil bath/water bath/oven). To this water is introduced with mixing, for example, mechanical stirring or sonication. The temperature is maintained high until self-assembly of all the polymer to form nanoparticles is confirmed by DLS analysis. In case of low (room) temperature, self-assembly still occurs. However the time taken was longer. Standard techniques using nano-separation is employed to estimate loading and encapsulation efficiency. The resultant solvent-free polymer nano-encapsulated suspension of the active compound could be directly applied or post processed using ultrafiltration or freeze drying or spray drying.

Figure 6:
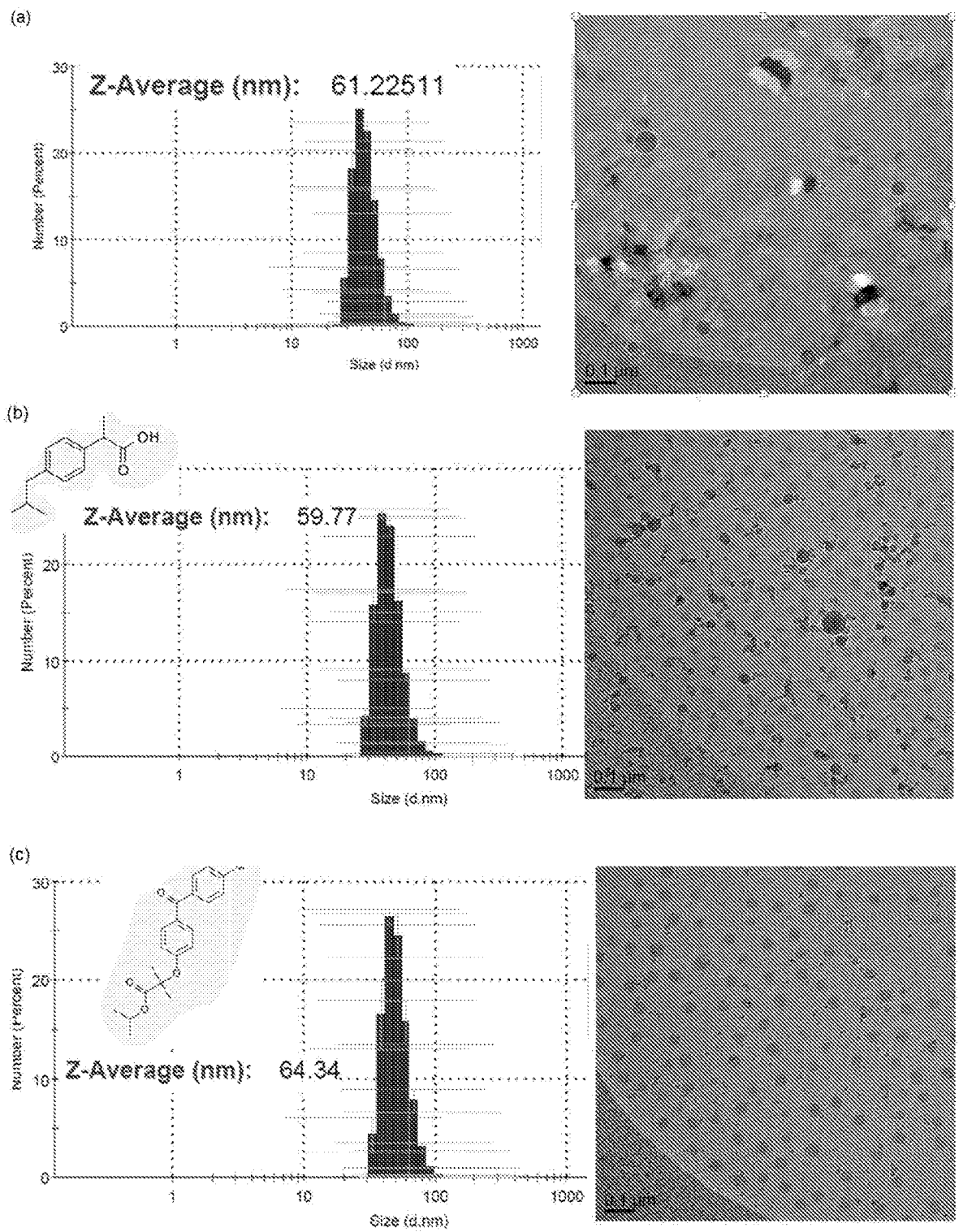
FIG. 6 shows polymer particle formation and encapsulation of actives by solvent free approach: a) Polymer only, b) Polymer+Ibuprofen, c) Polymer+Fenofibrate.

For comparison purpose, a polymer particle experiment without the API was conducted. Particle size determination by DLS clearly showed nanometer sized monodisperse particles. Upon using Ibuprofen or fenofibrate as API, monodisperse particles was obtained, which were confirmed by both DLS experiments and cryo-Transmission electron microscopy (FIG. 6).

Table 3 shows a list of exemplary hydrophobic actives encapsulated by various block co-polymers using present method.

TABLE 3

List Of Actives Encapsulated In Biodegradable Polymer Particles Using Present Solvent-Free Method And Their Applications

| Name of Active/ Polymer | Weight % of Active in the polymer nanoparticle | Size of Polymeric nanoparticle (nm) | PDI | Application |
|---|---|---|---|---|
| Ibuprofen/PEG-PCL | 20.0 | 77.3 | 0.229 | Controlled release |
| Ibuprofen/PEG-PLGA | 10.0 | 129.2 | 0.239 | Controlled release |
| Fenofibrate/PEG-PCL | 20.0 | 64.3 | | Controlled release |
| Ketoconazole/Peg-PCL | 10.0 | 80.4 | 0.233 | Controlled release |
| PM2 Peptide/PEG-PCL | 5.0 | 68.6 | 0.117 | Controlled release |
| Citronellalol/PEG-PCL | 20.0 | 87.8 | 0.141 | Personal care topical |
| Citronellalol/PEG-PCL | 30.0 | 76.8 | 0.080 | Personal care topical |
| Citronellalol/PEG-PCL | 50.0 | 119.2 | 0.218 | Personal care topical |
| IsoTretinoin PEG/PCL | 2.0 | 121.3 | 0.404 | Personal care topical |
| IsoTretinoin PEG/PLGA | 2.1 | 247.1 | 0.229 | Personal care topical |

Preliminary Release Studies

Figure 7:
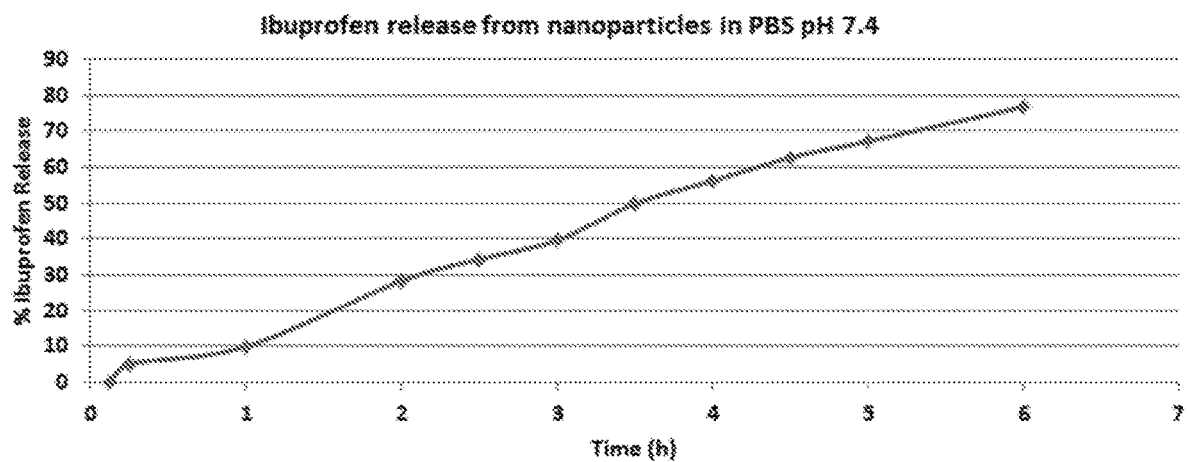
FIG. 7 shows Ibuprofen release profile as determined by HPLC analysis according to one example.

Results on the particle formation motivated a study to see the release of active from the encapsulated nanoparticles in order to evaluate the application potential of these particles and understand the extent of stabilization of the API in the encapsulate. A typical release profile obtained for Ibuprofen encapsulated using the solvent-free approach is given in FIG. 7.

From the preliminary release profile presented, it is very clear that the polymer encapsulate formed by this approach is efficient in stabilizing large amount of API in an aqueous environment well above its solubility limit and controlling its release.

Mechanism of Particle Formation

This experiment aims to study the self-assembly properties of PEG-PCL particles, by slowing down the process of encapsulation and studying samples taken at regular intervals. The mechanism study was conducted with both drugs used in the examples.

Ibuprofen was first used to study the self-assembly of PEG-PCL particles. Ideally, PEG-PCL should assemble into a micelle-like structure due to its amphiphilic properties.

Figure 8:
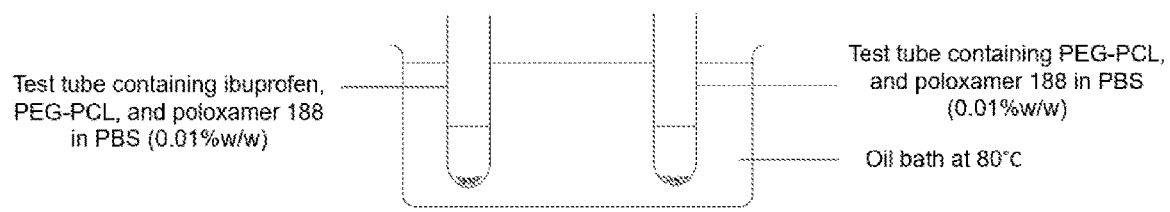
FIG. 8 shows a set-up of mechanism study for ibuprofen.

The mechanism study was conducted without the aid of agitation, and only using heat. FIG. 8 gives a schematic diagram of the set-up.

Ibuprofen and PEG-PCL were weighed in the 20% drug ratio (previously concluded to be most optimum) for the loaded sample, and the same amount of PEG-PCL was weighed for the blank sample as well. Both samples were melted in the oil bath, together with the poloxamer 188 in PBS (0.01% w/w).

Figure 9:
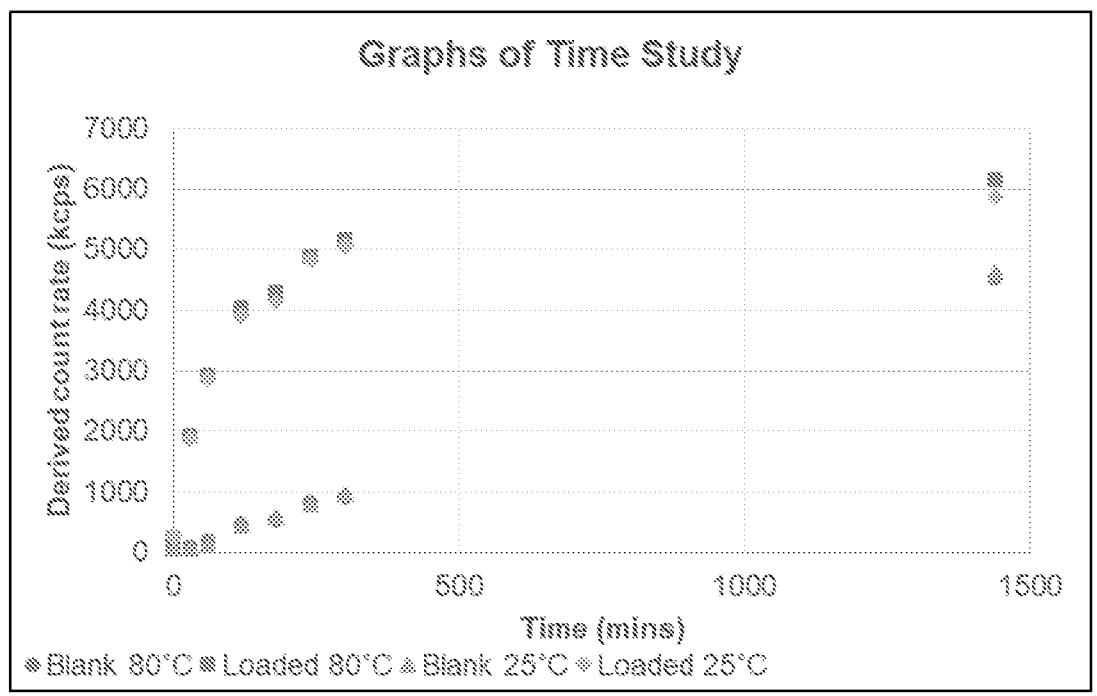
FIG. 9 shows a graph of derived count rate against time, for mechanism study of ibuprofen.

Samples were taken every 15 mins for the first hour and every hour for subsequent 5 hours and analysed by DLS. Samples were analysed at 80° C. and 25° C. FIG. 9 shows the trend of derived count rate with respect to time.

As seen from the trends above, the count rate (number of particles present) increased as time progresses. This means that particles are being formed continuously, and reaches a plateaus after a point in time. It can be observed that the particles loaded with ibuprofen formed particles much faster than those of blank particles. It is clear that the drug is aiding in the formation of particles, as they bring the polymer into the aqueous phase. Hence, this experiment proves that the present finding of solvent-free nanoparticle formation is a spontaneous self-assembly.

CONCLUSION

The results presented in this example clearly illustrate a new method for encapsulation of drugs with high loading in biodegradable matrix to give nanometer sized delivery system. The method provides an efficient, safe, versatile and economic alternative to currently available techniques and opens up avenues for application in pharma, consumer care and agrochemicals.

By "comprising" it is meant including, but not limited to, whatever follows the word "comprising". Thus, use of the term "comprising" indicates that the listed elements are required or mandatory, but that other elements are optional and may or may not be present.

By "consisting of" is meant including, and limited to, whatever follows the phrase "consisting of". Thus, the phrase "consisting of" indicates that the listed elements are required or mandatory, and that no other elements may be present.

The inventions illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

By "about" in relation to a given numerical value, such as for temperature and period of time, it is meant to include numerical values within 10% of the specified value.

The invention has been described broadly and generically herein. Each of the narrower species and sub-generic groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

The invention claimed is:

1. A solvent-free method of encapsulating a hydrophobic active in personal care, hydrophobic active in crop protection or a hydrophobic active pharmaceutical ingredient (API) in polymeric nanoparticles, the method comprising:
    mixing the hydrophobic active in a polymer melt, wherein the polymer melt consists of a melt of a block co-polymer, wherein the polymer melt acts as a solvent for the hydrophobic active;
    dispersing the polymer melt having the hydrophobic active solubilized therein in solely water; and
    maintaining the polymer melt in water for sufficient time to allow self-assembly of the polymeric nanoparticles spontaneously occurring in the polymer melt, wherein the self-assembly of the polymeric nanoparticles comprises encapsulation of the hydrophobic active in the polymeric nanoparticles.

2. The method of claim 1, further comprising cooling the self-assembled dispersion to enhance the stabilization of the hydrophobic active encapsulated in the polymeric nanoparticles.

3. The method of claim 1, wherein the hydrophobic active is dissolved at a temperature above the melting temperature of the block co-polymer.

4. The method of claim 1, wherein the polymer melt is dispersed in water at 0 to 50° C. higher than the melting temperature of the block co-polymer.

5. The method of claim 1, wherein the polymer melt is maintained in water at 50° C. or lower.

6. The method of claim 2, wherein the polymer melt is cooled to room temperature and below to aid storage and to enhance stabilization of the nanoparticles formed.

7. The method of claim 6, wherein the polymeric nanoparticles formed are cooled to room temperature.

8. The method of claim 2, wherein the polymer melt is cooled at a rate of 0.25 to 1.5° C./min.

9. The method of claim 1, further comprising stirring the dispersion of the polymer melt in water to enhance the self-assembly process, wherein the dispersion is stirred at a stirring rate of 50 rpm or higher.

10. The method of claim 1, wherein the block co-polymer comprises a diblock co-polymer of poly (ethylene glycol)-poly-lactic acid, poly(ethylene glycol-poly(glycolic acid), poly(ethylene glycol)-poly-lactic-co-glycolic acid, poly(ethylene glycol)-poly(butyl cyano-acrylate), poly(ethylene glycol)-block-poly hydroxybutyrate), poly(ethylene glycol)-poly-(hydroxypropionate), poly-(ethylene glycol)-(Valero lactone), poly(ethylene glycol)-poly(caprolactone) (PEG-PCL), poly-(ethylene glycol)-poly-(benzyl asparatate), poly-(ethylene glycol)-poly-(benzyl glutamate), poly(ethylene glycol)-poly-benzyloxy trimethylene carbonate, poly (ethylene glycol)-poly-butadiene, poly(ethylene glycol)-poly-(butyl acrylate), or a tri-block copolymer.

11. The method of claim 10, wherein the block co-polymer comprises a PEG block of 1,500 to 15,000 Da.

12. The method of claim 10, wherein the block co-polymer comprises a PCL block of 3,500 to 24,000 Da.

13. The method of claim 1, wherein the hydrophobic active comprises of a compound in various therapeutic classes selected from the group consisting of beta-adrenoceptor blocking agents, contrast media, corticosteroids, cough suppressants, diagnostic agents, diagnostic imaging agents, diuretics, dopaminergics, haemostatics, immunological agents, lipid regulating agents, muscle relaxants, parasympathomimetics, parathyroid calcitonin, prostaglandins, radio-pharmaceuticals, sex hormones, anti-allergic agents, stimulants, sympathomimetics, thyroid agents, vasodilators, xanthines, analgesics, anti-inflammatory agents, anthelmintics, anti-arrhythmic agents, antibiotics, anticoagulants, antidepressants, antidiabetic agents, antiepileptics, antihistamines, antihypertensive agents, antimuscarinic agents, antimycobacterial agents, antineoplastic agents, immunosuppressants, antithyroid agents, antiviral agents, anxiolytic sedatives and astringents.

14. The method of claim 13, wherein the hydrophobic active comprises ibuprofen, fenofibrate, ketoconazole, PM2 peptide, citronellal, itraconazole, isotretinoin, β-carotene, retinal, retinoic acid, curcumin, doxorubicin, SN-38, paclitaxel, camptothecin, cisplatin, daunorubicin, methotrexate, mitomycin C, docetaxel, vincristine, amphotericin B, nystatin, prostaglandins, cyfluthrin, butanilicaine, fomocaine, isobutambene, lidocaine, risocaine, pseudococaine, prilocaine, tetracaine, trimecaine, tropacocaine, etomidate, metixen, profenamine, alimenazine, binedaline, perazine, chlorpromazine, fenpentadiol, mebenazine, methylphenidate, thioridazine, toloxatone, trimipramide, dimethadione, nicethamide, butoconazole, chlorphenesin, etisazole, exalamide, miconazole, butibufen, azinphosphomethyl, cypermethrin, substituted phenyl thiophosphates, permethrin, piperonal, tetramethrine, trifluraline, penclomedine, trofosfamide, capsaicin, methylnicotinate, nicolclonate, oxprenolol, pirifibrate, simfibrate, thiadenol, aminopromazine, difemerine, fencarbamide, tiropramide, moxaverine, testosterone enantate, testosterone-(4-methylpentanoate), azaperone, buramate, arildone, retinol, retinol acetate, retinol palmitate, tocopherol acetate, tocopherol succinate, tocopherol nicotinate, menadione, cholecalciferol, acephate bamifylline, alprenolol, butobendine, clordiazole, hexobendine, nicofibrate, penbutolol, pirmenol, prenylamine, procaine amide, propatrylnitrate, suloctidil, toliprolol, viquidil, asperline, chlorambucile, mitotane, estramustine, taxol, or macrolide antibiotics.

15. The method of claim 1, wherein the hydrophobic active comprises a crop protecting agent or a personal care agent.

16. The method of claim 15, wherein the crop protecting agent comprises pyrethrins.

* * * * *